United States Patent [19]
Bryant et al.

[11] Patent Number: 5,981,570
[45] Date of Patent: Nov. 9, 1999

[54] BENZOTHIOPHENE COMPOUNDS, COMPOSITIONS, AND METHODS

[75] Inventors: Henry Uhlman Bryant, Indianapolis; George Joseph Cullinan, Trafalgar; Jeffrey Alan Dodge, Indianapolis, all of Ind.

[73] Assignee: Eli Lilly and Company, Indianapolis, Ind.

[21] Appl. No.: 08/935,374

[22] Filed: Sep. 22, 1997

Related U.S. Application Data

[60] Provisional application No. 60/027,449, Sep. 27, 1996.

[51] Int. Cl.$^6$ .................. A61K 31/38; A61K 31/425; A61K 31/44
[52] U.S. Cl. .................. 514/432; 514/337; 514/365; 514/369; 514/443; 546/281.1; 548/203; 548/204; 549/13; 549/49; 549/57; 549/28
[58] Field of Search ................... 549/13, 49, 57, 549/28; 546/281.1; 548/203, 204; 574/337, 365, 432, 443, 369

[56] References Cited

U.S. PATENT DOCUMENTS

| | | | |
|---|---|---|---|
| 3,394,125 | 7/1968 | Crenshaw | 260/326.5 |
| 3,413,305 | 11/1968 | Crenshaw | 260/326.5 |
| 4,133,814 | 1/1979 | Jones et al. | 260/326 |
| 4,230,862 | 10/1980 | Suarez et al. | 546/237 |
| 4,358,593 | 11/1982 | Jones et al. | 546/202 |
| 4,380,635 | 4/1983 | Peters | 546/202 |
| 4,418,068 | 11/1983 | Jones et al. | 546/237 |
| 5,395,842 | 3/1995 | Labrie | 514/320 |
| 5,470,854 | 11/1995 | Angerer et al. | 514/233 |
| 5,472,962 | 12/1995 | Koizumi et al. | 514/233.5 |
| 5,514,703 | 5/1996 | Carlson et al. | 514/443 |
| 5,532,382 | 7/1996 | Carlson et al. | 549/57 |
| 5,596,106 | 1/1997 | Cullinan et al. | 549/57 |

FOREIGN PATENT DOCUMENTS

| | | |
|---|---|---|
| 062 503 | 10/1982 | European Pat. Off. . |
| 709090 | 5/1996 | European Pat. Off. . |
| WO 89/0289 | 4/1989 | WIPO . |
| WO 95/10513 | 4/1995 | WIPO . |
| 9602248 | 2/1996 | WIPO . |

OTHER PUBLICATIONS

Crenshaw, R.R., et al, *J. Med. Chem.* 14(12):1185–1190 (1971).
Jones, C.D., et al. *J. Med. Chem.* 27: 1057–1066) 1984.
Jones, C.D., et al, *J. Med. Chem.* 35: 931–938 1992.

*Primary Examiner*—Amelia Owens
*Attorney, Agent, or Firm*—Gilbert T. Voy

[57] ABSTRACT

The invention provides benzothiophene compounds, formulations, and methods of inhibiting bone loss or bone resorption, particularly osteoporosis, cardiovascular-related pathological conditions, including hyperlipidemia.

18 Claims, No Drawings

BENZOTHIOPHENE COMPOUNDS, COMPOSITIONS, AND METHODS

This application claims the benefit of U.S. Provisional Application No. 60/027,449 filed on Sep. 27, 1996.

BACKGROUND OF THE INVENTION

Osteoporosis describes a group of diseases which arises from diverse etiologies, but which are characterized by the net loss of bone mass per unit volume. The consequence of this loss of bone mass and resulting bone fracture is the failure of the skeleton to provide adequate support for the body. One of the most common types of osteoporosis is associated with menopause. Most women lose from about 20% to about 60% of the bone mass in the trabecular compartment of the bone within 3 to 6 years after the cessation of menses. This rapid loss is generally associated with an increase of bone resorption and formation. However, the resorptive cycle is more dominant and the result is a net loss of bone mass. Osteoporosis is a common and serious disease among postmenopausal women.

There are an estimated 25 million women in the United States alone who are afflicted with this disease. The results of osteoporosis are personally harmful, and also account for a large economic loss due to its chronicity and the need for extensive and long term support (hospitalization and nursing home care) from the disease sequelae. This is especially true in more elderly patients.

Additionally, although osteoporosis is generally not thought of as a life threatening condition, a 20% to 30% mortality rate is related to hip fractures in elderly women. A large percentage of this mortality rate can be directly associated with postmenopausal osteoporosis.

The most vulnerable tissue in the bone to the effects of postmenopausal osteoporosis is the trabecular bone. This tissue is often referred to as spongy or cancellous bone and is particularly concentrated near the ends of the bone (near the joints) and in the vertebrae of the spine. The trabecular tissue is characterized by small osteoid structures which interconnect with each other, as well as the more solid and dense cortical tissue which makes up the outer surface and central shaft of the bone. This interconnected network of trabeculae gives lateral support to the outer cortical structure and is critical to the biomechanical strength of the overall structure. In postmenopausal osteoporosis, it is primarily the net resorption and loss of the trabeculae which leads to the failure and fracture of bone. In light of the loss of the trabeculae in the postmenopausal woman, it is not surprising that the most common fractures are those associated with bones which are highly dependent on trabecular support, for example, the vertebrae, the neck of the weight-bearing bones such as the femur and the forearm. Indeed, hip fracture, collies fractures, and vertebral crush fractures are hallmarks of postmenopausal osteoporosis.

The most generally accepted method for the treatment of postmenopausal osteoporosis is estrogen replacement therapy. Although therapy is generally successful, patient compliance with the therapy is low, primarily because estrogen treatment frequently produces undesirable side effects. An additional method of treatment would be the administration of a bisphosphonate compound, such as, for example, Fosamax® (Merck & Co., Inc.).

Throughout premenopausal time, most women have less incidence of cardiovascular disease than men of the same age. Following menopause, however, the rate of cardiovascular disease in women slowly increases to match the rate seen in men. This loss of protection has been linked to the loss of estrogen and, in particular, to the loss of estrogen's ability to regulate the levels of serum lipids. The nature of estrogen's ability to regulate serum lipids is not well understood, but evidence to date indicates that estrogen can up regulate the low density lipid (LDL) receptors in the liver to remove excess cholesterol. Additionally, estrogen appears to have some effect on the biosynthesis of cholesterol, and other beneficial effects on cardiovascular health.

It has been reported in the literature that serum lipid levels in postmenopausal women having estrogen replacement therapy return to concentrations found in the premenopausal state. Thus, estrogen would appear to be a reasonable treatment for this condition. However, the side effects of estrogen replacement therapy are not acceptable to many women, thus limiting the use of this therapy. An ideal therapy for this condition would be an agent which regulates serum lipid levels in a manner analogous to estrogen, but which is devoid of the side effects and risks associated with estrogen therapy.

In response to the clear need for new pharmaceutical agents which are capable of alleviating the symptoms of, inter alia, postmenopausal syndrome, the instant invention provides novel benzo[b]thiophene compounds, pharmaceutical formulations thereof, and methods of using such compounds for the treatment of postmenopausal syndrome and other estrogen-related pathological conditions.

SUMMARY OF THE INVENTION

The present invention relates to compounds of formula I:

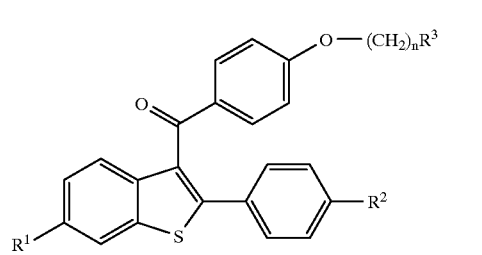

wherein:
$R^1$ is —H, —OH, —O($C_1$-$C_4$ alkyl), —OCO($C_1$-$C_6$ alkyl), —O(CO)O($C_1$-$C_6$ alkyl), —OCOAr, —O(CO)OAr, where Ar is phenyl or optionally substituted phenyl, or —OSO$_2$($C_2$-$C_6$ alkyl);
$R^2$ is —H, —OH, —O($C_1$-$C_4$ alkyl), —OCO($C_1$-$C_6$ alkyl), —O(CO)O($C_1$-$C_6$ alkyl), —OCOAr, —O(CO)OAr, where Ar is phenyl or optionally substituted phenyl, or —OSO$_2$($C_2$-$C_6$ alkyl);
$R^3$ is —CH$_3$, thiophenyl, thiazolyl or optionally substituted thiazolyl, phenyl or optionally substituted phenyl, 2-pyridyl, 3-pyridyl, 4-pyridyl, or cyclohexyl; and
n is 0 to 10;
with the proviso that when $R^3$ is —CH$_3$, then n is 2 to 10; or a pharmaceutically acceptable salt or solvate thereof.

The present invention further relates to pharmaceutical compositions containing compounds of formula I, and the use of said compounds at least the inhibition of bone loss or bone resorption, particularly osteoporosis, cardiovascular-related pathological conditions, including hyperlipidemia.

DETAILED DESCRIPTION OF THE INVENTION

General terms used in the description of compounds herein described bear their usual meanings. For example, "$C_1$–$C_6$ alkyl" refers to straight or branched aliphatic chains of 1 to 6 carbon atoms including methyl, ethyl, propyl, isopropyl, butyl, n-butyl, pentyl, isopentyl, hexyl, isohexyl, and the like. Similarly, the term "—$OC_1$–$C_4$ alkyl" represents a $C_1$–$C_4$ alkyl group attached through an oxygen such as, for example, methoxy, ethoxy, n-propoxy, isopropoxy, and the like. Of these $C_1$–$C_4$ alkoxy groups, methoxy is highly preferred.

The term "substituted phenyl" refers to a phenyl group having one or more substituents selected from the group consisting of $C_1$–$C_4$ alkyl, —$OC_1$–$C_4$ alkyl, hydroxy, nitro, chloro, fluoro, or tri(chloro or fluoro)methyl.

The term "hydroxy protecting group" contemplates numerous functionalities used in the literature to protect a hydroxyl function during a chemical sequence and which can be removed to yield the phenol. Included within this group would be acyls, mesylates, tosylates, benzyl, alkylsilyloxys, $C_1$–$C_4$ alkyls, and the like. Numerous reactions for the formation and removal of such protecting groups are described in a number of standard works including, for example, *Protective Groups in Organic Chemistry*, Plenum Press (London and New York, 1973); Green, T. W., *Protective Groups in Organic Synthesis*, Wiley, (New York, 1981); and *The Peptides*, Vol. I, Schrooder and Lubke, Academic Press (London and New York, 1965). Methods for removing preferred hydroxy protecting groups, particularly methyl and alkylsilyloxy, are essentially as described in the Examples, infra.

The term "leaving group" means a chemical entity which is capable of being displaced by an amino function via an $SN_2$ reaction. Such reactions are well known in the art and such groups would include halogens, mesylates, tosylates, and the like. A preferred leaving group would be bromo.

The term "solvate" represents an aggregate that comprises one or more molecules of the solute, such as a formula I compound, with one or more molecules of solvent.

The term "inhibit" includes its generally accepted meaning which includes prohibiting, preventing, restraining, and slowing, stopping, or reversing progression, severity, or ameliorating a resultant symptom or effect.

The compounds of this invention are derivatives of centrally located carbon, for example, the "—CO—", "—CHOH—", or "—$CH_2$—" moiety in formula I are therefore derivatives of methanones, methanols, or methanes. For example, a compound of A—CO—B, would be named [A][LB]methanone. Further, the compounds of formula I are derivatives of benzo[b]thiophene which is named and numbered according to the Ring Index, The American Chemical Society, as follows:

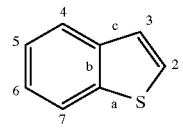

Compounds of formula I include:
[6-Methoxy-2-(4-methoxyphenyl)benzo[b]thien-3-yl][4-(2-(cyclohexyl)ethoxy]phenyl]methanone;
[6-Methoxy-2-(4-methoxyphenyl)benzo[b]thien-3-yl][4-(n-hexyloxy]phenyl]methanone;
[6-Hydroxy-2-(4-hydroxyphenyl)benzo[b]thien-3-yl][4-(2-(cyclohexyl)ethoxy]phenyl]methanone;
[6-Methoxy-2-(4-methoxyphenyl)benzo[b]thien-3-yl][4-[3-(pyridyl)methoxy]phenyl]methanone;
[6-Hydroxy-2-(4-hydroxyphenyl)benzo[b]thien-3-yl][4-[3-(pyridyl)methoxy]phenyl]methanone;
[6-Methoxy-2-(4-methoxyphenyl)benzo[b]thien-3-yl][4-[4-(pyridyl)methoxy]phenyl]methanone;
[6-Hydroxy-2-(4-hydroxyyphenyl)benzo[b]thien-3-yl][4-[4-(pyridyl)methoxy]phenyl]methanone;
[6-Methoxy-2-(4-methoxyphenyl)benzo[b]thien-3-yl][4-[2-(pyridyl)methoxy]phenyl]methanone;
[6-Hydroxy-2-(4-hydroxyphenyl)benzo[b]thien-3-yl][4-[2-(pyridyl)methoxy]phenyl]methanone;
[6-Methoxy-2-(4-methoxyphenyl)benzo[b]thien-3-yl][4-[3-(thiophenyl)methoxy]phenyl]methanone;
[6-Methoxy-2-(4-methoxyphenyl)benzo[b]thien-3-yl][4-[2-(4-methyl-5-thiazolyl)ethoxy]phenyl]methanone;
[6-Hydroxy-2-(4-hyroxyphenyl)benzo[b]thien-3-yl][4-[2-(4-methyl-5-thiazolyl)ethoxy]phenyl]methanone;
[6-Hydroxy-2-(4-hydroxyphenyl)benzo[b]thien-3-yl][4-(n-hexyloxy]phenyl]methanone;
[6-Methoxy-2-(4-methoxyphenyl)benzo[b]thien-3-yl][4-(n-propoxy]phenyl]methanone;
[6-Hydroxy-2-(4-hydroxyphenyl)benzo[b]thien-3-yl][4-(n-propoxy]phenyl]methanone;
[6-Methoxy-2-(4-methoxyphenyl)benzo[b]thien-3-yl][4-(n-butyloxy]phenyl]methanone;
[6-Hydroxy-2-(4-hydroxyphenyl)benzo[b]thien-3-yl][4-(n-butyloxy]phenyl]methanone;
[6-Hydroxy-2-(4-hydroxyphenyl)benzo[b]thien-3-yl][4-(n-decyloxy]phenyl]methanone;
[6-Methoxy-2-(4-methoxyphenyl)benzo[b]thien-3-yl][4-[4-(fluoro)benzyloxy]phenyl]methanone;
[6-Methoxy-2-(4-methoxyphenyl)benzo[b]thien-3-yl][4-[4-(methoxy)benzyloxy]phenyl]methanone;
[6-Methoxy-2-(4-methoxyphenyl)benzo[b]thien-3-yl][4-[2-(4-methoxy)phenyl]ethoxy]phenyl]methanone;
[6-hydroxy-2-(4-hydroxyphenyl)benzo[b]thien-3-yl][4-[2-(4-hydroxy)phenyl]ethoxy]phenyl]methanone, and the like.

Preferred compounds include
[6-Hydroxy-2-(4-hydroxyphenyl)benzo[b]thien-3-yl][4-(2-(cyclohexyl)ethoxy]phenyl]methanone and
[6-Hydroxy-2-(4-hydroxyphenyl)benzo[b]thien-3-yl][4-[3-(pyridyl)methoxy]phenyl]methanone.

The starting compounds for the compounds of the present invention are prepared according to established procedures, such as those detailed in U.S. Pat. Nos. 4,133,814 and 4,418,068, the disclosures of which are herein incorporated by reference. See, also, Jones et al. *J. Med. Chem*, 27, 1057 (1984). In general, the process starts with a benzo[b]thiophene having a 6-hydroxyl group and a 2-(4-hydroxyphenyl) group. The starting compound is protected and optionally deprotected to form the formula I compounds. Further formula I compounds may then be formed as desired. Specific preparations of compounds of the present invention are described herein. Modifications to the above methods may be necessary to accommodate reactive functionalities of particular substituents. Such modifications would be both apparent to, and readily ascertained by, those skilled in the art. Scheme I further illustrates the preparation of compounds of formula I.

Scheme I

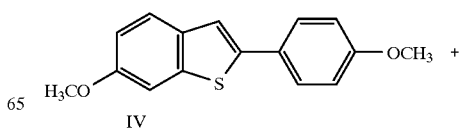

IV

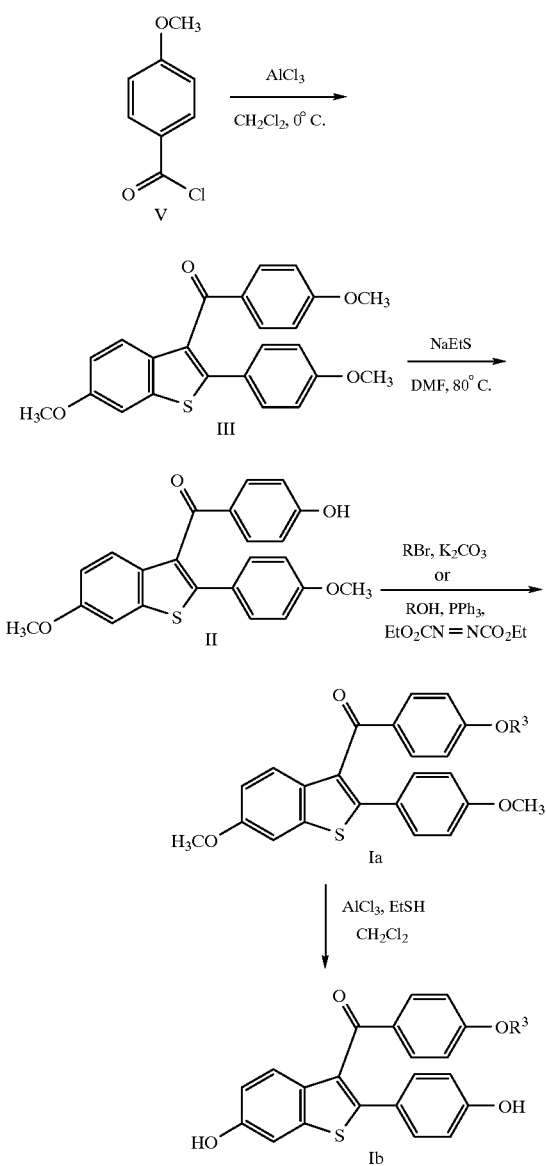

In order to substitute with different groups of $R_1$ and $R_2$, one of the positions is protected with a hydroxy protecting group. The term "hydroxy-protecting group" refers to readily cleavable groups bonded to hydroxy groups, such as the tetrahydropyranyl, 2-methoxyprop-2-yl, 1-ethoxyeth-1-yl, methoxymethyl, β-methoxyethoxymethyl, methylthiomethyl, t-butyl, t-amyl, trityl, 4-methoxytrityl, 4,4'-dimethoxytrityl, 4,4',4"-trimethoxytrityl, benzyl, allyl, trimethylsilyl, (t-butyldimethylsilyl, and 2,2,2-trichloroethoxycarbonyl groups, and the like. For example, treatment of a compound of formula IV with one equivalent of t-butyldimethylsilyl chloride and an appropriate amount of base results in a statistical mixture of 4'- and 6- silyl protected phenols, which can then be separated by chromatography.

The species of hydroxy-protecting groups is not critical so long as the derivatized hydroxyl group is stable to the conditions of subsequent reaction(s) and can be removed at the appropriate point without disrupting the remainder of the reaction.

Further examples of hydroxy-protecting groups are described by C. B. Reese and E. Haslam, *Protective Groups in Organic Chemistry*, J. G. W. McOmie, Ed., Plenum Press, New York, N.Y., 1973, Chapters 3 and 4, and T. W. Greene, *Protective Groups in Organic Synthesis*, John Wiley and Sons, New York, N.Y., 1981, Chapters 2 and 3. The monohydroxy-protected compound is then subjected to the reaction conditions as described previously. Thereafter, the protected hydroxy is de-protected and a different substituent may be placed thereon.

Although the free-base form of formula I compounds can be used in the methods of the instant invention, it is preferred to prepare and use a pharmaceutically acceptable salt form. The term "pharmaceutically acceptable salt" refers to either acid or base addition salts which are known to be non-toxic and are commonly used in the pharmaceutical literature. The pharmaceutically acceptable salts generally have enhanced solubility characteristics compared to the compound from which they are derived, and thus are often more amenable to formulation as liquids or emulsions. The compounds used in the methods of this invention primarily form pharmaceutically acceptable acid addition salts with a wide variety of organic and inorganic acids, and include the physiologically acceptable salts which are often used in pharmaceutical chemistry. Such salts are also part of this invention.

Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl-substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caproate, caprylate, chloride, cinnamate, citrate, formate, fumarate, glycolate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or ethyl acetate. The salt normally precipitates out of solution within about one hour to 10 days and can be isolated by filtration, or the solvent can be stripped off by conventional means. The instant invention further provides for pharmaceutically acceptable formulations for administering to a mammal, including humans, in need of treatment, which comprises an effective amount of a compound of formula I and a pharmaceutically acceptable diluent or carrier.

As used herein, the term "effective amount" means an amount of compound of the instant invention which is capable of inhibiting bone loss or bone resorption, particularly osteoporosis, and cardiovascular-related pathological conditions including hyperlipidemia and related cardiovascular pathologies.

By "pharmaceutically acceptable formulation" it is meant that the carrier, diluent, excipients and salt must be compatible with the active ingredient (a compound of formula I) of the formulation, and not be deleterious to the recipient thereof. Pharmaceutical formulations can be prepared by procedures known in the art. For example, the compounds of this invention can be formulated with common excipients, diluents, or carriers, and formed into tablets, capsules, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as agar agar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate and solid polyethylene glycols. Final pharmaceutical forms may be: pills, tablets, powders, lozenges, syrups, aerosols, saches, cachets, elixirs, suspensions, emulsions, ointments, suppositories, sterile injectable solutions, or sterile packaged powders, and the like, depending on the type of excipient used.

Additionally, the compounds of this invention are well suited to formulation as sustained release dosage forms. The formulations can also be so constituted that they release the active ingredient only or preferably in a particular part of the intestinal tract, possibly over a period of time. Such formulations would involve coatings, envelopes, or protective matrices which may be made from polymeric substances or waxes.

The particular dosage of a compound of formula I required to inhibit the symptoms and/ or disease of a mammal, including humans, suffering from the above maladies according to this invention will depend upon the particular disease, symptoms, and severity. Dosage, routes of administration, and frequency of dosing is best decided by the attending physician. Generally, accepted and effective doses will be from 15 mg to 1000 mg, and more typically from 15 mg to 80 mg, one to three times per day. Such dosages will be administered to a patient in need thereof usually at least for thirty days, and more typically for six months, or chronically.

The formulations which follow are given for purposes of illustration and are not intended to be limiting in any way. The total active ingredients in such formulations comprises from 0.1% to 99.9% by weight of the formulation. The term "active ingredient" means a compound of formula I.

Formulation 1

Gelatin Capsules

| Ingredient | Quantity (mg/capsule) |
| --- | --- |
| Active Ingredient | 0.1–1000 |
| Starch NF | 0–500 |
| Starch flowable powder | 0–500 |
| Silicone fluid 350 centistokes | 0–15 |

The ingredients are blended, passed through a No. 45 mesh U.S. sieve, and filled into hard gelatin capsules.

Formulation 2

Tablets

| Ingredient | Quantity (mg/tablet) |
| --- | --- |
| Active Ingredient | 2.5–1000 |
| Starch | 10–50 |
| Cellulose, microcrystalline | 10–20 |
| Polyvinylpyrrolidone (as 10% solution in water) | 5 |
| Sodium carboxymethylcellulose | 5 |
| Magnesium stearate | 1 |
| Talc | 1–5 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules thus produced are dried at 50–60° C. and passed through a No. 18 mesh U.S. sieve. The sodium carboxymethylcellulose, magnesium stearate, and talc, previously passed through a No. 60 mesh U.S. sieve, are added to the above granules and thoroughly mixed. The resultant material is compressed in a tablet forming machine to yield the tablets.

Formulation 3

Aerosol

| Ingredient | Weight % |
| --- | --- |
| Active Ingredient | 0.25 |
| Ethanol | 29.75 |
| Propellant 22 | 70.00 |
| (Chlorodifluoromethane) | |
| Total | 100.00 |

The active ingredient is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Suppositories

| Ingredient | Weight |
| --- | --- |
| Active ingredient | 150 mg |
| Saturated fatty acid glycerides | 3000 mg |

The active ingredient is passed through a No. 60 mesh U.S. sieve and suspended in the fatty acid glycerides which had previously heated to their melting point. The mixture is poured into a suppository mold and allowed to cool.

Formulation 5

Suspension

Suspensions each containing 0.1–1000 mg of a compound of formula I per 5 mL dose.

| Ingredient | Weight |
| --- | --- |
| Active Ingredient | 0.1–1000 mg |
| Sodium carboxymethyl cellulose | 50 mg |
| Syrup | 1.25 mL |
| Benzoic acid solution (0.1 M) | 0.10 mL |
| Flavor | q.v. |
| Color | q.v. |
| Purified water to total | Total 5 mL |

A compound of formula I is passed through a No. 45 mesh U.S. sieve and mixed with the sodium carboxymethyl cellulose and syrup to form a smooth paste. The benzoic acid solution, flavor, and color diluted in water are added and mixture stirred thoroughly. Additional water is added to bring the formulation to final volume.

The following Examples and Preparations are provided to better elucidate the practice of the instant invention and should not be interpreted in any way as to limit the scope of same. Those skilled in the art will recognize that various modifications may be made while not departing from the spirit and scope of the invention. All publications and patent applications mentioned in the specification are indicative of the level of those skilled in the art to which this invention pertains.

NMR data for the following Examples were generated on a GE 300 MHz NMR instrument, and anhydrous $CDCl_3$ was used as the solvent unless otherwise indicated. Field strength for $^{13}C$ NMR spectra was 75.5 MHz, unless otherwise indicated.

All experiments were run under positive pressure of dry nitrogen. All solvents and reagents were used as obtained. The percentages are generally calculated on a weight (w/w) basis; except for HPLC solvents which are calculated on a volume (v/v) basis. Proton nuclear magnetic resonance ($^1H$ NMR) spectra were obtained on a Bruker AC-300 FTNMR spectrometer at 300.135 MHz. Melting points were determined and are reported uncorrected.

EXAMPLES

Preparation 1

[6-Methoxy-2-(4-methoxyphenyl)benzo[b]thien-3-yl](4-methoxyphenyl)methanone

To a solution of p-anisoyl chloride (1.54 g, 9.00 mmol) stirring in anhydrous $CH_2Cl_2$ (100 mL) was added a compound of formula IV (1.62 g, 6.00 mmol) all at once as a solid. The resulting suspension was cooled to 0° C. and $AlCl_3$ (1.20 g, 9.00 mmol) was added in small portions over a five minute period. After 1 h, the dark reaction mixture was poured into ice water (150 mL) and extracted with $CH_2Cl_2$ (3×75 mL). The organic extracts were combined and washed with NaOH (30 mL of a 1N aq. solution), water (25 mL), and brine (25 mL). The organic layers were then dried ($MgSO_4$) and the mixture concentrated. The resulting crude product was purified by flash chromatography (silica gel, 30% EtOAc in hexanes) to give 2.25 g (93%) of a light yellow solid. The product was further purified by recrystallization from acetone/methanol to give 2.11 g (87%): $^1H$ NMR (300 MHz, DMSO-$d_6$) δ7.64–7.69 (m, 3H), 7.29–7.32 (m, 3H). 6.86–7.00 (m, 5H), 3.83 (s, 3H) 3.76 (s, 3H); $^{13}C$ NMR (75.5 MHz, DMSO-$d_6$) δ192, 163.6, 159.4, 157.3, 141, 139.3, 133.1, 131.8, 130, 129.6, 125.1, 123.2, 115.0, 114.3, 114.0, 105.1, 55.4, 55.1; IR ($CHCl_3$) 3020, 3015, 2970, 2940, 2840, 1600, 1475, 1253, 1218, 1167 $cm^{-1}$; MS (FD) 404 (M+); Calcd for $C_{24}H_{20}O_4S$: C, 71.27; H, 4.98; S, 7.93; O, 15.82. Found: C, 71.50; H, 5.00; S, 7.98; O, 15.77.

Preparation 2

[6-Methoxy-2-(4-methoxyphenyl)benzo[b]thien-3-yl](4-hydroxyphenyl)methanone

To the compound exemplified in Preparation 1 (0.40 g, 1.00 mmol) stirring in dry DMF (2 mL) was added EtSNa (3.0 mL of 0.50M solution in DMF). The reaction temperature was heated to 80° C. After 4 h, the mixture was diluted with EtOAc (10 mL) and water (10 mL). The mixture was then neutralized with 1N HCl and extracted with EtOAc (3×20 mL). The combined organic extracts were washed with brine (4×20 mL.), dried ($MgSO_4$), filtered, and concentrated to give a pale yellow solid. The solid was further purified by radial chromatography (2 mm, silica gel, 5% EtOAc in $CH_2Cl_2$) to give 0.31 g (79%) of a foamy yellow solid: $^1H$ NMR (300 MHz, $CDCl_3$) δ7.70–7.73 (d, 2H, J=8.6 Hz), 7.52–7.55 (d, 1H, J=8.5 Hz), 7.31–7.34 (m, 3H), 6.94–6.98 (dd, 1H, J=9.0 Hz, J=2.4 Hz), 6.73–6.76 (d, 2H, J=8.7 Hz), 6.66–6.69 (d, 2H, J=9.1 Hz), 3.88 (s, 3H), 3.74 (S, 3H) ; $^{13}C$ NMR (75.5 MHz $CDCl_3$) δ192.9, 159.9, 158.5, 156.5, 141.9, 138.9, 132.7, 131.7, 129.12, 129.1, 128.8, 124.7, 122.8, 114.3, 113.7, 112.9, 103.4, 54.5, 54.1; IR ($CHCl_3$) 3585, 3265, 3022, 3012, 2970, 2940, 2840, 1602, 1476, 1254, 1163 $cm^{-1}$; MS (FD) 390 (M+); EA calcd for $C_{23}H_{18}O_4S$: C, 70.75; H, 4.65. Found: C, 70.93; H, 4.56.

Example 1

[6-Methoxy-2-(4-methoxyphenyl)benzo[b]thien-3-yl][4-(2-(cyclohexyl)ethoxy]phenyl]methanone To the compound exemplified in Preparation 2 (0.97 g, 2.50 mmol) and triphenylphosphine (1.31 g, 5.00 mmol) stirring in THF (50 mL) at room temperature was added 2-cyclohexylethanol (0.70 mL, 5.0 mmol) followed by diethyl azodicarboxylate (DEAD) (0.79 ml, 5.0 mmol). After 2 h, the reaction was concentrated and the resulting solid purified by radial chromatography (silica gel, 4 mm, 17:3 hexanes: $NEt_3$) to give 1.01 g (81%) of the desired product: IR ($CHCl_3$) 3012, 2928, 1855, 1599, 1476, 1254, 1166 $cm^{-1}$; $^1H$ NMR (300 MHz, $CDCl_3$) δ7.75–7.78 (d, 2H, J=8.8 Hz), 7.49–7.52 (d, 1H, J=8.9 Hz), 7.31–7.36 (m, 3H), 6.93–6.96 (dd, 1H, J=8.9 Hz, J=2.2 Hz), 6.73–6.78 (m, 4H), 3.95–3.99 (t, 2H, J=6.7 Hz), 3.88 (s, 3H), 3.74 (s, 3H), 0.83–1.80 (13H); MS (FD) 500 (M+)

Example 2

[6-Methoxy-2-(4-methoxyphenyl)benzo[b]thien-3-yl][4-(n-hexyloxy]phenyl]methanone To the compound exemplified in Preparation 2 (1.17 g, 3.00 mmol) stirring in DMF (20 ml) at room temperature was added ground $K_2CO_3$ (1.035 g, 7.50 mmol) and the mixture heated to 100° C. After 15 minutes, 1-bromohexane (4.21 ml, 30 mmol) was added and the reaction was stirred for an additional 1 h at 100° C. The mixture was cooled to room temperature and filtered. The filtrate was diluted with water (25 ml) and extracted with EtOAc (3×20 ml). The combined organic extracts were washed with brine (3×20 ml), dried ($MgSO_4$), filtered, and concentrated to give 1.36 g (96%) of desired product: IR ($CHCl_3$) 3011, 2959, 2937, 1599, 1476, 1254, 1166 $cm^{-1}$; $^1H$ NMR (300 MHz, $CDCl_3$) δ7.76–7.79 (d, 2H, J=9 Hz), 7.50–7.53 (d, 1H, J=9 Hz), 7.34–7.37 (d, 2H, J=9 Hz), 7.31–7.32 (d, 1H, J=2 Hz), 6.93–6.96 (dd, 1H, J=9 Hz, J=2 Hz), 6.73–6.77 (m, 4H), 3.90–3.95 (t, 2H, J=6.5 Hz), 3.86 (s, 3H), 3.74 (s, 3H), 1.68–1.78 (m, 2H), 1.26–1.46 (m, 6H), 0.86–0.90 (t, 3H, J=6.5 Hz); $^{13}$C NMR (75.5 MHz, CDCl$_3$) δ193.3, 163.4, 159.7, 157.6, 142.3, 140.1, 134.7, 132.4, 130.7, 130.2, 130.2, 126.1, 124.1, 114.8, 114.1, 114.1, 104.5, 68.2, 55.6, 55.2, 31.5, 29.0, 25.6, 22.6, 14.0; MS (FD) 474 (M+); Anal. calcd. for C$_{29}$H$_{30}$O$_4$S: C, 73.39; H, 6.37; Found: C, 73.66; H, 6.30.

Example 3

[6-Hydroxy-2-(4-hydroxyphenyl)benzo[b]thien-3-yl] [4-(2-(cyclohexyl)ethoxy]phenyl]methanone To the compound of Example 1 (1.01 g, 2.01 mmol) stirring in CH$_2$Cl$_2$ (30 ml) at room temperature was added AlCl$_3$ (1.68 g, 12.1 mmol) followed by EtSH (0.78 ml, 11 mmol). The reaction was vigorously stirred for 30 minutes and then quenched with sodium bicarbonate. Any undissolved residue was taken up with MeOH. This mixture was then extracted with EtOAc (3×20 ml) and the combined organic extracts washed with brine (4×20 ml), dried (MgSO$_4$), filtered, and concentrated. Purification of the resulting material by radial chromatography (4 mm, silica gel, 14/5/1 of hexanes/EtOAc/MeOH) afforded 0.67 g (71) of product as an off-white solid: IR (CHCl$_3$) 3357, 2923, 2848, 1587, 1449, 1252, 1163; $^1$H NMR (300 MHz, MeOHd$_4$) δ7.67–7.70 (d, 2H, J=8.6 Hz), 7.37–7.40 (d, 1H, J=8.8 Hz), 7.24–7.25 (d, 1H, J=2.3 Hz), 7.17–7.20 (d, 2H, J=8.7 Hz), 6.83–6.87 (dd, 1H, J=8.8 Hz, J=2.1 Hz), 6.78–6.81 (d, 2H, J=8.7 Hz), 6.61–6.64 (d, 2H, J=9.0 Hz), 3.97–4.01 (t, 2H, J=6.6 Hz), 0.90–1.80 (m, 13 H); MS (FD) 472 (M+).

Example 4

[6-Methoxy-2-(4-methoxyphenyl)benzo[b]thien-3-yl][4-[3-(pyridyl)methoxy]phenyl]methanone Reaction of the compound of Preparation 2 (1.5 g, 3.7 mmol), 3-pyridilcarbinol (0.5 g, 4.6 mmol), PPh$_3$ (1.2 g, 4.6 mmol) and DEAD (0.8 g, 4.6 mmol) in THF (150 mL) at 25° C. for 48 h according to the procedure described in Example 3 provided a quantitative yield of 312871 as a yellow oil: $^1$H-NMR(300 MHz, DMSO-d$_6$) δ7.41–7.80 (complex, 8H), 7.38–7.39 (m, 1H), 7.27–7.33 (m, 2H), 6.96–7.03 (m, 2H), 6.85–6.88(d, J=9.0 Hz, 2H), 5.15 (s, 2H), 3.82 (s, 3H) 3.68 (s, 3H); MS (FD) 481 (M+).

Example 5

[6-Hydroxy-2-(4-hydroxyphenyl)benzo[b]thien-3-yl] [4-[3-(pyridyl)methoxy]phenyl]methanone Reaction of a compound of Example 4 (2.75 g, 4.42 mmol), AlCl$_3$ (4.60 g, 34.3 mmol), EtSH (2.13 g, 34.3 mmol), CH$_2$Cl$_2$ (200 mL) at 25° C. for 0.5 h according to the procedure described in Example 3 gave a 41% yield of the desired product as a yellow solid: IR (KBr) 3292, 1597, 1571, 1536,1507, 1437, 1382, 1355, 1309, 1264, 1168, 1126, 1032, 907, 839, 808 cm$^{-1}$; $^1$H-NMR (300 MHz, DMSOd$_6$) δ9.86 (br s, 2H), 8.62–8.63(s, 1H), 8.52–8.53 (m, 1H), 7.81–7.84 (d, 1H, J=8.0 Hz), 7.64–7.68 (m, 2H), 7.37–7.41 (m, 1H), 7.32 (s, 1H), 7.22–7.32 (d, J=9.0 Hz, 1H), 7.12–7.16 (complex, 2H), 6.99 (d, 2H, J=8.8 Hz), 6.81–6.82 (complex, 1H), 6.65 (d, 2H, J=8.6 Hz), 5.14 (s, 2H); MS(FD) 454 (M+); Anal. Calcd. for C$_{27}$H$_{19}$NO$_4$S: C,71.51; H, 4.22; N, 3.09. Found: C, 71.65; H, 4.23; N, 3.17.

Example 6

[6-Methoxy-2-(4-methoxyphenyl)benzo[b]thien-3-yl][4-[4-(pyridyl)methoxy]phenyl]methanone Reaction of the compound of Preparation 2(2.0 g, 5.2 mmol),4-pyridilcarbinol (0.7 g, 6.5 mmol), PPh$_3$ (1.7 g, 6.5 mmol), and DEAD (1.13 g, 6.5 mmol) in THF (150 mL), at 25° C. for 4 h according to the procedure described in Example 3 provided a quantitative yield of the desired product as a yellow oil: $^1$H-NMR(300 MHz, DMSO-d$_6$) δ7.59–7.62 (complex, 3H),7.26–7.38 (complex, 7H), 6.96–7.06 (complex, 3H), 6.86 (d, J=9.1 Hz, 2H), 5.19 (s, 2H), 3.69 (s, 3H), 3.82 (s, 3H) 3.69 (s, 3H); MS (FD) 481 (M+).

Example 7

[6-Hydroxy-2-(4-hydroxyyphenyl)benzo[b]thien-3-yl][4-[4-(pyridyl)methoxy]phenyl]methanone Reaction of the compound of Example 6(4.63 g, 9.60 mmol), AlCl$_3$ (7.70 g, 57.7 mmol) and EtSH (3.60 g, 57.7 mmol in CH$_2$Cl$_2$ (250 mL) at 25° C. for 0.5 h according to the procedure described in Example 3 gave a 27% yield of the desired product as a yellow solid: IR (KBr) 1640, 1597, 1536, 1502, 1468, 1420, 1353, 1258, 1166, 1119, 1035, 907, 834, 807, 723, 694, 541 cm$^{-1}$; $^1$H-NMR (300 MHz, DMSO-d$_6$) d 9.64 (s, 1H), 9.73 (s, 1H), 8.54 (d, 2H, J=9.0 Hz), 7.50–7.67 (complex, 2H), 7.36–7.38 (complex, 2H) 7.32 (s, 1H), 7.24–7.25 (complex, 1H), 7.14 (d, 2H, J=8.5 Hz), 6.97 (d, 2H, J=8.8 Hz), 6.84 (m 1H), 6.63–6.66 (d, 2H, J=8.9 Hz), 5.19 (s, 2H); MS (FD) 454 (M+); Anal. Calcd. for C$_{27}$H$_{19}$NO$_4$S: C, 71.51; H, 4.22; N, 3.09. Found: C, 71.27; H, 4.22; N, 3.00.

Example 8

[6-Methoxy-2-(4-methoxyphenyl)benzo[b]thien-3-yl][4-[2-(pyridyl)methoxy]phenyl]methanone Reaction of the compound of Preparation 2(1.23 g, 3.2 mmol), 2-pyridylcarbinol (0.44 g, 4.0 mmol), PPh$_3$ (1.1 g, 4.0 mmol) and DEAD (0.7 g, 4.0 mmol) in THF (150 mL) at 25° C. for 48 h according to the procedure described in Example 3 provided a quantitative yield of the desired product as a yellow oil: $^1$H-NMR(300 MHz, DMSO-d$_6$) d 7.29–7.64 (complex, 8H), 7.33–7.37 (complex, 4H), 6.88–7.02 (complex, 2H), 6.85 (d, J=9.0 Hz,1H), 5.18 (s, 2H), 3.81 (s, 3H), 3.75 (s, 3H); MS (FD) 481 (M+).

Example 9

[6-Hydroxy-2-(4-hydroxyphenyl)benzo[b]thien-3-yl] [4-[2-(pyridyl)methoxy]phenyl]methanone Reaction of Example 8 (2.13 g, 4.42 mmol), AlCl$_3$ (3.54 g, 26.6 mmol) and EtSH (1.62 g, 26.0 mmol) in CH$_2$Cl$_2$ (200 mL) at 25° C. for 0.5 h according to the procedure described in Example 3 gave a 85% yield of the desired product as a yellow solid: IR (KBr) 3294, 2891, 1711, 1641, 1597, 1573, 1537, 1503, 1458, 1348, 1264, 1229, 1166, 1061, 1036, 835 cm$^{-1}$; $^1$H-NMR (300 MHz, DMSO-d$_6$) d 9.70 (s, 1H), 9.90 (s, 1H), 7.50–7.70 (complex, 8H), 7.43 (d,1H, J=2.3 Hz), 7.37–7.39 (m, 1H), 7.22–7.24 (d, 1H, J=9.0 Hz), 7.13–7.20 (d, 1H), 6.99–7.20(d, 1H, J=8.9 Hz), 6.82–6.84 (m, 1H), 6.63–6.40 (d, 1H, J=9.0 Hz), 5.20 (s, 2H), MS(FD) 453 (M+); Anal. Calcd. for C$_{27}$H$_{19}$NO$_4$S: C, 71.51; H, 4.22; N, 3.09. Found: C, 71.53; H, 4.50; N, 3.32.

Example 10

[6-Methoxy-2-(4-methoxyphenyl)benzo[b]thien-3-yl][4-[3-(thiophenyl)methoxy]phenyl]methanone Reaction of the compound of Preparation 2 (0.39 g, 1.00 mmol), PPh$_3$ (0.39 g, 1.50 mmol), 3-thiophenemethanol (0.24 ml, 1.50 mmol) and DEAD (0.14 ml, 1.50 mmol) in THF (5 mL) according to the procedure described in Example 3 provided a 77% yield of the desired product as a yellow oil: $^1$H-NMR (300 MHz, CDCl$_3$) δ7.78 (d, J=8.5 Hz, 2H), 7.54 (d, J=8.9 Hz, 1H), 7.29–7.38 (complex, 4H), 7.10 (d, J=8.7 Hz, 1H), 6.96 (dd, J=8.8 Hz, 2.4 Hz, 1H), 6.84 (d, J=8.8 Hz, 2H), 6.77 (d, j=8.8 Hz, 2H), 5.07 (s, 2H), 3.90 (s, 3H), 3.77 (s, 3H); IR (CHCl$_3$) 1646, 1599 cm$^{-1}$; MS (FD) 486 (M+).

Example 11

[6-Methoxy-2-(4-methoxyphenyl)benzo[b]thien-3-yl][4-[2-(4-methyl-5-thiazaolyl)ethoxy]phenyl]methanone Reaction of a compound of Preparation 2 (0.39 g, 1.00 mmol), PPh$_3$ (0.39 g, 1.50 mmol) 4-methyl-5-thiazaole-ethanol (0.18 ml, 1.50 mmol) and DEAD (0.14 ml, 1.50 mmol) in THF (5 mL) according to the procedure described in Example 3 provided a 77% yield of the desired product as a yellow oil: $^1$H-NMR (300 MHz, CDCl$_3$) δ8.60 (s, 1H), 7.77 (d, J=8.7 Hz, 2H), 7.52 (d, J=8.9 Hz, 1H), 7.31–7.36 (complex, 3H), 6.97 (dd, J=9.0, 2.4 Hz, 1H), 6.75(d, J=9.0 Hz, 4H), 4.12 (d, J=3.6 Hz, 2H), 3.90 (s, 3H), 3.74 (s, 3H), 3.22 (t, J=3.5 Hz, 2H), 2.43 (s, 3H).

Example 12

[6-Hydroxy-2-(4-hyroxyphenyl)benzo[b]thien-3-yl][4-[2-(4-methyl-5-thiazaolyl)ethoxy]phenyl]methanone Reaction of a compound of Example 11 (0.27 g, 0.52 mmol), AlCl$_3$ (0.42 g, 3.12 mmol) and EtSH (0.19 mL, 2.6 mmol) in CH$_2$Cl$_2$ (10 mL) at room temp. for 0.5 h. according to the procedure described in Example 3 provided a 95% of the desired product as a yellow solid: $^1$H-NMR (300 MHz, CDCl$_3$) δ9.91 (s, 1H), 9.71 (s, 1H), 8.82 (s, 1H), 7.67 (d, J=8.7 Hz, 2H), 7.35 (d, J=2.3 Hz, 1H), 7.26 (d, J=8.8 Hz, 1H), 7.18 (d, J=8.9 Hz, 2H), 6.93 (d, J=8.7 Hz, 2H), 6.86 (dd, J=8.9, 2.3 Hz, 1H), 6.66 (d, J=8.8 hz, 2H), 4.19 (t, J=3.3 Hz, 2H), 3.20 (t, J=3.6 Hz, 2H), 2.32 (s, 3H); IR (thin film) 3299, 1700, 1635 cm–1; MS (FD) 488 (M+) Anal. calcd. for C$_{25}$H$_{21}$O$_4$NS$_2$; calc'd/found C(66.51/66.88), H (4.34/4.49), N (2.88/2.95).

Example 13

[6-Hydroxy-2-(4-hydroxyphenyl)benzo[b]thien-3-yl][4-(n-hexyloxy)phenyl]methanone Reaction of a compound of Example 2 (1.20 g, 2.54 mmol), AlCl$_3$ (2.03 g, 15.2 mmol) and EtSH (12.7 mmol) in CH$_2$Cl$_2$ (50 mL) at room temp. for 0.5 h according to the procedure described in Example 3 provided a 86% of the desired product as a yellow solid: IR (CHCl$_3$) 3357, 2956, 2928, 1597, 1252, 1164 cm$^{-1}$; $^1$H NMR (300 MHz, MeOH-d$_4$) δ7.67–7.70 (d, 2H, J=8.7 Hz), 7.37–7.40 (d, 1H, J=8.8 Hz), 7.24–7.25 (d, 1H, J=2.1 Hz), 7.17–7.20 (d, 2H, J=8.6 Hz), 6.85 (dd, 1H, J=8.7 Hz, J=2.3 Hz), 6.79 (d, 2H, J=8.9 Hz), 6.63 (d, 2H, J=8.9 Hz), 3.96 (t, 2H, J=6.4 Hz), 1.68–1.77 (m, 2H), 1.30–1.45 (m, 6H), 0.85 (t, 3H, J=6.6 Hz); $^{13}$C NMR (62.9 MHz, MeOH-d$_4$) δ195.7, 165.1, 159.1, 156.7, 143.7, 141.4, 134.3, 133.5, 131.3, 126.1, 124.7, 116.5, 116.0, 115.2, 107.9, 69.4, 32.6, 30.1, 26.7, 23.6, 14.4; MS (FD) 446 (M+).

Example 14

[6-Methoxy-2-(4-methoxyphenyl)benzo[b]thien-3-yl][4-(n-propoxy)phenyl]methanone

Reaction of a compound of Preparation 2 (1.17 g, 3.00 mmol), K$_2$CO$_3$ (1.03 g, 7.50 mmol) and 1-bromopropane (2.73 ml, 30 mmol) in DMF (20 mL) at 100° C. for 40 min according to the procedure described in Example 2 provided a 80% of the desired product as a yellow oil: IR (CHCl$_3$) 3011, 2974, 2944, 1599, 1476, 1254, 1166 cm$^{-1}$; $^1$H NMR (300 MHz, CDCl$_3$) δ7.75–7.78 (d, 2H, J=8.7 Hz), 7.49–7.52 (d, 1H, J=8.8 Hz), 7.33–7.36 (d, 2H, J=8.9 Hz), 7.31–7.32 (d,1H, J=2.7 Hz), 6.93–6.97 (dd, 1H, J=9.1 Hz, J=2.7 Hz), 6.73–6.78 (m, 4H), 3.88–3.92 (t, 2H, J=6.6 Hz), 3.87 (s, 3H), 3.74 (s, 3H), 1.72–1.83 (m, 2H), 0.98–1.03 (t, 3H, J=7.4 Hz); $^{13}$C NMR (75.5 MHz, CDCl$_3$) δ193.3, 163.4, 159.7, 157.7, 142.2, 140.0, 134.0, 132.4, 130.7, 130.2, 130.2, 126.1, 124.1, 114.8, 114.1, 114.1, 104.5, 69.67, 55.6, 55.2, 22.4, 10.4; MS (FD) 432 (M+); Anal. calcd. for C$_{26}$H$_{24}$O$_4$S: C, 72.20; H, 5.59; Found: C, 72.00; H, 5.65.

Example 15

[6-Hydroxy-2-(4-hydroxyphenyl)benzo[b]thien-3-yl][4-(n-propoxy)phenyl]methanone

Reaction of a compound of Example 14 (0.86 g, 2.00 mmol), AlCl$_3$ (1.60 g, 12.0 mmol) and EtSH (10 mmol) in CH$_2$Cl$_2$ (50 mL) at room temp for 0.5 h according to the procedure described in Example 3 provided a 91% yield of the desired product as a yellow solid: IR (CHCl$_3$) 3333, 3020, 2958, 1597, 1468, 1265, 1239, 1168; $^1$H NMR (300 MHz, MeOHd$_4$) δ7.68–7.71 (d, 2H, J=8.9 Hz), 7.39 (d, 1H, J=8.7 Hz), 7.24 (d, 1H, J=2.5 Hz), 7.17–7.20 (d, 2H, J=8.6 Hz), 6.84–6.87 (dd, 1H, J=8.8, 2.3 Hz), 6.81 (d, 2H, J=8.9 Hz), 6.61–6.64 (d, 2H, J=8.5 Hz), 3.94 (t, 2H, J=6.5 Hz), 1.70–1.80 (m, 2H), 0.99 (t, 3H, J=7.4 Hz); $^{13}$C NMR (75.5 MHz, MeOH-d$_4$) δ195.0, 164.4, 158.4, 156.0, 143.0, 140.7, 133.6, 132.7, 130.6, 125.3, 123.9, 115.7, 115.3, 114.5, 107.1, 70.1, 22.6, 9.9; MS (FD) 405 (M+).

Example 16

[6-Methoxy-2-(4-methoxyphenyl)benzo[b]thien-3-yl][4-(n-butyloxy)phenyl]methanone Reaction of a compound of Preparation 2 (1.17 g, 3.00 mmol), K$_2$CO$_3$ (1.04 g, 7.50 mmol) and 1-iodobutane (3.41 mL, 30 mmol) in DMF (20 mL) at 100° C. for 40 min according to the procedure described in Example 2 provided a 77% yield of the desired product as a yellow oil: IR (CHCl$_3$) 3011, 2963, 2938, 1599, 1476, 1254, 1166; $^1$H NMR (300 MHz, CDCl$_3$) δ7.74–7.77 (d, 2H, J=9 Hz), 7.50 (d, 1H, J=9 Hz), 7.34 (d, 2H, J=9 Hz), 7.31 (d, 1H, J=2.5 Hz), 6.93–6.96 (dd, 1H, J=9.0, 2.5 Hz), 6.73–6.78 (m, 4H), 3.94 (t, 2H, 7.0 Hz), 3.88 (s, 3H), 3.74 (s, 3H), 1.69–1.79 (m, 2H), 1.40–1.50 (m, 2H), 0.95 (t, 3H, J=7.0 Hz); $^{13}$C NMR (75.5 MHz, CDCl$_3$) δ193.3, 163.4, 159.7, 157.6, 142.3, 140.0, 134.0, 132.4, 130.6, 130.2, 130.1, 126.0, 124.0, 114.8, 114.1, 114.1, 104.5, 67.9, 55.6, 55.2, 31.0, 19.1, 13.8; MS (FD) 446 (M+).

Example 17

[6-Hydroxy-2-(4-hydroxyphenyl)benzo[b]thien-3-yl][4-(n-butyloxy)phenyl]methanone Reaction of a compound of Example 16 (0.89 g, 2.00 mmol), AlCl$_3$ (1.60 g, 12.0 mmol) and EtSH (10 mmol) in CH$_2$Cl$_2$ (50 mL) at room temp. for 0.5 h according to the procedure described in Example 3 provided a 79% yield of the desired product as a yellow solid: IR (CHCl$_3$) 3344, 3116, 3025, 2958, 1598, 1254, 1168 cm$^{-1}$; $^1$H NMR (300 MHz, MeOH-d$_4$) δ7.68 (d, 2H, J=8.6 Hz), 7.38 (d, 1H, J=8.8 Hz), 7.24 (d, 1H, J=2.3 Hz), 7.19 (d, 2H, J=8.5 Hz), 6.86 (dd, 1H, J=8.7, 2.3 Hz), 6.79 (d, 2H, J=8.8 Hz), 6.63 (d, 2H, J=8.5 Hz), 3.95 (t, 2H, J=6.4 Hz), 1.68–1.75 (m, 2H), 1.41–1.51 (m, 2H), 0.95 (t, 3H, J=7.4 Hz); $^{13}$C NMR (75.5 MHz,MeOH-d$_4$) δ194.9, 164.3, 158.4, 155.9, 142.8, 140.6, 133.5, 132.6, 130.5, 130.4, 125.2, 123.8, 115.6, 115.2, 114.4, 107.1, 68.2, 31.3, 19.3, 13.2; MS (FD) 419 (M+); Anal. calcd. for $C_{25}H_{22}O_4S$: C, 71.75; H, 5.30; Found: C, 71.95; H, 5.54.

Example 18

[6-Hydroxy-2-(4-hydroxyphenyl)benzo[b]thien-3-yl][4-(n-decyloxy)phenyl]methanone Reaction of a compound of Preparation 2 (1.17 g, 3.00 mmol), $K_2CO_3$ (1.04 g, 7.50 mmol) and 1-iododecane (6.40 mL, 30 mmol) in DMF (20 mL) at 100° C. for 40 min gave a quantiative yield of the desired product which was subjected to deprotection reaction conditions without further purification. Thus, reaction with $AlCl_3$ (2.3 g, 17.0 mmol) and EtSH (14.1 mmol) in $CH_2Cl_2$ (50 ml) at room temp. for 0.5 h according to the procedure described in Example 7 provided a 70% of the desired product as a yellow solid: IR (CHCl$_3$) 3300, 2929, 2857, 1598, 1469, 1262, 1166; $^1$H NMR (300 MHz, MeOHd$_4$) δ7.68 (d, 2H, J=9 Hz), 7.38 (d, 1H, J=9.0 Hz), 7.24 (d, 1H, J=2 Hz), 7.17 (d, 2H, J=9.1 Hz), 6.87(dd, 1H, J=9, 2 Hz), 6.80 (d, 2H, J=9 Hz), 6.63 (d, 2H, J=9 Hz), 3.94 (t, 2H, J=6 Hz), 1.68–1.76 (m, 2H), 1.25–1.46 (m, 14H), 0.88 (t, 3H, J=6 Hz); $^{13}$C NMR (75.5 MHz, DMSO-d$_6$) δ 192.5, 162.9, 157.8, 155.4, 140.2, 139.2, 132.3, 131.8, 129.7, 129.6, 129.5, 123.8, 123.3, 115.6, 115.1, 114.3, 107.1, 67.8, 31.2, 28.9, 28.9, 28.7, 28.6, 28.4, 25.3, 22.0, 13.9; MS (FD) 502 (M+); Anal. calcd. for $C_{31}H_{34}O_4S$: C, 74.07; H, 6.82; Found: C, 73.85; H, 6.94.

Example 19

[6-Methoxy-2-(4-methoxyphenyl)benzo[b]thien-3-yl][4-[4-(fluoro)benzyloxy]phenyl]methanone The compound exemplified in Preparation 2 (0.75 g, 1.92 mmol) was dissolved in 15 ml DMF and this solution was stirred at 100° C. for 10–15 min. $K_2CO_3$ (0.53 g, 3.84 mmol) and p-fluorobenzyl chloride (0.83 g, 5.76 mmol) were then added and the reaction was stirred at 100° C. for 1.5 hrs. While hot, the $K_2CO_3$ was filtered off and rinsed with hot EtOAc (10 ml). The solvent was evaporated and the resulting tan-yellow oil was purified by rotary chromatography (silica gel, 25% EtOAc/Hex) to give 0.869 g (91%) of a yellow oil. IR (CHCl$_3$)3016, 2960, 2940, 1645, 1600, 1514, 1476, 1253, 1166, 1157, 1048, 1034, 832 cm$^{-1}$; $^1$H NMR (300 MHz, CDCl$_3$) δ7.78–7.81 (d, 2H, J=8.9 Hz), 7.53–7.56 (d, 1H, J=8.5 Hz), 7.33–7.39 (m, 5H), 7.05–7.10 (app t, 2H, J=7.5 Hz), 6.95–6.99 (dd, 1H, J=8.4 Hz, J=1.8 Hz), 6.82–6.85 (d, 2H, J=9.0 Hz), 6.76–6.79 (d, 2H, J=8.8 Hz), 5.01 (s, 2H), 3.90 (s, 3H), 3.76 (s, 3H); $^{13}$C NMR (75.481 MHz, CDCl$_3$) δ193.19, 162.65, 159.77, 157.69, 142.65, 140.08, 132.38, 130.75, 130.51, 130.31, 129.44, 129.32, 126.03, 124.07, 115.75, 115.46, 114.83, 114.44, 114.08, 104.95, 104.51, 69.39, 55.63, 55.26; FD+ MS for $C_{30}H_{23}FO_4S$=498; Anal. calcd. for $C_{30}H_{23}FO_4S$: C, 72.27; H, 4.65; Found: C, 71.36; H, 4.74.

Example 20

[6-Methoxy-2-(4-methoxyphenyl)benzo[b]thien-3-yl][4-[4-(methoxy)benzyloxy]phenyl]methanone A compound of Preparation 2 (1.00 g, 2.56 mmol) was dissolved in 15 ml DMF and the solution was stirred at 100° C. for 10 minutes followed by the addition of $K_2CO_3$ (0.708 g, 5.12 mmol) and benzyl chloride (1.203 g, 7.68 mmol). The reaction was stirred at 100° C. for 2 hrs, at which time the $K_2CO_3$ was filtered off while the reaction was still hot. The solvent was evaporated to give a tan-yellow oil which was purified by rotary chromatography (silica gel, 25% EtOAc/Hex) to give 0.778 g (84%) of a yellow oil. IR (CHCl$_3$)n$_{max}$ 3015, 1645, 1599, 1517, 1476, 1251, 1179, 1166, 1035, 832; $^1$H NMR (300 MHz, DMSO) d 7.78–7.81 (d, 2H, J=9 Hz), 7.52–7.55 (d, 1H, J=9 Hz), 7.30–7.38 (m, 5H), 6.95–6.99 (dd, 1H, J=9 Hz; J=2.1 Hz), 6.90–6.93 (d, 2H, J=8.7 Hz), 6.83–6.86 (d, 2H, J=8.5 Hz), 6.76–6.79 (d, 2H, J=8.7HZ), 4.98 (s, 2H), 3.90 (s, 3H), 3.82 (S, 3H), 3.77 (s, 3H); $^{13}$C NMR (75.481 MHz, CDCl$_3$) d 193.31, 162.98, 159.75, 159.66, 157.66, 142.46, 140.07, 134.01, 132.36, 130.60, 130.51, 130.27, 129.30, 128.07, 126.04, 124.07, 114.79, 114.47, 114.08, 104.50, 69.92, 55.63, 55.29, 55.25; FD+ MS for $C_{31}H_{26}O_5S$=510; Anal. calcd. for $C_{31}H_{26}O_5S$: C, 72.92; H, 5.13; Found: C, 72.33; H, 5.20.

Example 21

[6-Methoxy-2-(4-methoxyphenyl)benzo[b]thien-3-yl][4-[2-(4-methoxy)phenyl]ethoxy]phenyl] methanone To a stirring solution of p-methoxyphenethyl alcohol (0.974 g, 6.40 mmol) and anhydrous THF (20 ml), at room temperature, were added triphenylphosphine (1.34 g, 5.12 mmol) and diethyl azodicarboxylate (0.892 g, 5.12 mmol). This mixture was stirred for 5 min then the compound of Preparation 2 (1.00 g, 2.56 mmol) was added as a solid. The reaction stirred overnight at room temperature and was quenched with $H_2O$ (20 ml). The organic layer was separated and the aqueous phase was extracted with EtOAc (3×15 ml). The combined organic layer and extracts were washed with brine (3×30 ml), dried (MgSO$_4$), and evaporated to give a yellow oil which was purified by rotary chromatography (silica gel, $CH_2Cl_2$) to give 0.98 g (73%) of a yellow solid. IR (CHCl$_3$) 3016, 2960, 2940, 1646, 1600, 1514, 1476, 1252, 1179, 1166, 1048, 1033, 832 cm$^{-1}$; $^1$NMR (300 MHz, CDCl$_3$) δ7.75–7.78 (d, 2H, J=8.7 Hz), 7.51–7.54 (d, 1H, J=8.9 Hz), 7.34–7.37 (d, 2H, J=8.8 Hz), 7.32–7.33 (d, 1H, J=2.3 Hz), 7.16–7.19 (d, 2H, J=8.5 Hz), 6.94–6.98 (dd, 1H, J=8.9 Hz; J=2.4 Hz), 6.85–6.88 (d, 2H, J=8.6 Hz), 6.75–6.78 (d, 4H, J=8.7 Hz), 4.10–4.15 (t, 2H, J=7.1 Hz), 3.90 (s, 3H), 3.80 (s, 3H), 3.75 (s, 3H), 2.99–3.04 (t, 2H, J=7.0 Hz); $^{13}$C NMR (75.481 MHz, CDCl$_3$) δ193.22, 163.01, 159.73, 158.39, 157.64, 142.41, 140.05, 133.98, 132.34, 130.57, 130.35, 130.24, 129.93, 129.74, 126.01, 124.04, 114.77, 114.27, 114.15, 114.06, 113.96, 104.48, 69.03, 55.61, 55.23, 34.63; FD+ MS for $C_{32}H_{28}O_5S$=524; Anal. calcd. for $C_{32}H_{28}O_5S$: C, 73.26; H, 5.38; Found: C, 73.30; H, 5.18.

Example 22

[6-hydroxy-2-(4-hydroxyphenyl)benzo[b]thien-3-yl][4-[2-(4-hydroxy)phenyl]ethoxy]phenyl]methanone A compound of Example 21 (0.100 g, 0.19 mmol) was dissolved in dichloromethane (2 mL) followed by the addition of $AlCl_3$ (0.153 g, 1.15 mmol) with stirring at 25° C. This mixture stirred for 5 min and EtSH (0.060 g, 0.95 mmol) was added. After stirring for 30 min at 25° C. the reaction was quenched with sat'd NaHCO$_3$ (30 ml) and diluted with 50 ml EtOAc. The organic layer was removed and the aqueous layer was extracted with EtOAc (3×25 ml). The organic layer and extracts were combined and washed with sat'd NaHCO$_3$ (2×30 ml), H$_2$O (2×35 ml) and brine (2×50 ml), dried (MgSO$_4$), and evaporated to give a yellow oil. Rotary chromatography (silica gel, 25–75% EtOAc/Hex) gave a yellow oil which foamed upon vacuum drying to a yellow solid 0.090 g (98%). $^1$H NMR (300 MHz, DMSO) δ9.76 (s, 1H), 9.72 (s, 1H), 9.19 (s, 1H), 7.60–7.63 (d, 2H, J=8.7 Hz), 7.30–7.31 (app t, 1H), 7.20–7.23 (d, 1H, J=8.8 Hz), 7.12–7.15 (d, 2H, J=8.5 Hz), 7.03–7.06 (d, 2H, J=8.3 Hz), 6.86–6.89 (d, 2H, J=8.8 Hz), 6.79–6.83 (dd, 1H, J=8.8 Hz, J=2.2 Hz), 6.63–6.66 (d, 4H, J=8.5 Hz), 4.07–4.11 (t, 2H, J=6.8 Hz), 2.83–2.87 (t, 2H, J=6.7 Hz); $^{13}$C NMR (75.481 MHz, DMSO) d 192.69, 162.91, 162.45, 157.98, 156.03, 155.57, 140.54, 139.38, 132.45, 132.26, 132.98, 130.00, 129.85, 128.02, 123.95, 123.49, 115.86, 115.55, 115.27, 114.64, 107.28, 69.06, 34.04 FD+ MS for $C_{29}H_{22}O_5S$=482.

Test Procedures

In the examples illustrating the methods, a postmenopausal model was used in which effects of different treatments upon circulating lipids were determined.

Seventy-five day old female Sprague Dawley rats (weight range of 200 to 225 g) were obtained from Charles River Laboratories (Portage, Mich.). The animals were either bilaterally ovariectomized (OVX) or exposed to a Sham surgical procedure at Charles River Laboratories, and then shipped after one week. Upon arrival, they were housed in metal hanging cages in groups of 3 or 4 per cage and had ad libitum access to food (calcium content approximately 0.5%) and water for one week. Room temperature was maintained at 22.2°±1.7° C. with a minimum relative humidity of 40%. The photoperiod in the room was 12 hours light and 12 hours dark.

Dosing Regimen Tissue Collection. After a one week acclimation period (therefore, two weeks post-OVX) daily dosing with test compound was initiated. 17α-ethynyl estradiol or the test compound were given orally, unless otherwise stated, as a suspension in 1% carboxymethylcellulose or dissolved in 20% cyclodextrin. Animals were dosed daily for 4 days. Following the dosing regimen, animals were weighed and anesthetized with a ketamine:xylazine (2:1, V:V) mixture and a blood sample was collected by cardiac puncture. The animals were then sacrificed by asphyxiation with CO$_2$, the uterus was removed through a midline incision, and a wet uterine weight was determined.

Cholesterol Analysis. Blood samples were allowed to clot at room temperature for 2 hours, and serum was obtained following centrifugation for 10 minutes at 3000 rpm. Serum cholesterol was determined using a Boehringer Mannheim Diagnostics high performance cholesterol assay. Briefly the cholesterol was oxidized to cholest-4-en-3-one and hydrogen peroxide. The hydrogen peroxide was then reacted with phenol and 4-aminophenazone in the presence of peroxidase to produce a p-quinone imine dye, which was read spectrophotometrically at 500 nm. Cholesterol concentration was then calculated against a standard curve.

Uterine Eosinophil Peroxidase (EPO) Assay. Uteri were kept at 4° C. until time of enzymatic analysis. The uteri were then homogenized in 50 volumes of 50 mM Tris buffer (pH—8.0) containing 0.005% Triton X-100. Upon addition of 0.01% hydrogen peroxide and 10 mM O-phenylenediamine (final concentrations) in Tris buffer, increase in absorbance was monitored for one minute at 450 nm. The presence of eosonophils in the uterus is an indication of estrogenic activity of a compound. The maximal velocity of a 15 second interval was determined over the initial, linear portion of the reaction curve.

Source of Compound: 17α-ethynyl estradiol was obtained from Sigma Chemical Co., St. Louis, Mo.

Influence of Formula I Compounds on Serum Cholesterol and Determination of Agonist/Non-Agonist Activity Data presented in Table 1 below show comparative results among ovariectomized rats, rats treated with 17α-ethynyl estradiol (EE$_2$; an orally available form of estrogen), and rats treated with certain compounds of the instant invention. Although EE$_2$ caused a decrease in serum cholesterol when orally administered at 0.1 mg/kg/day, it also exerted a stimulatory action on the uterus so that EE$_2$ uterine weight was substantially greater than the uterine weight of ovariectomized test animals. This uterine response to estrogen is well recognized in the art.

Not only did the compounds of the instant invention generally reduce serum cholesterol compared to the ovariectomized control animals, but uterine weight was only minimally increased to slightly decreased with the majority of the formula compounds tested. Compared to estrogenic compounds known in the art, the benefit of serum cholesterol reduction without adversely affecting uterine weight is quite rare and desirable.

As is expressed in the data below, estrogenicity also was assessed by evaluating the adverse response of eosinophil infiltration into the uterus. The compounds of the instant invention did not cause any increase in the number of eosinophils observed in the stromal layer of ovariectomized rats, while estradiol cause a substantial, expected increase in eosinophil infiltration.

The data presented in Table 1 below reflects the response of 5 to 6 rats per treatment.

TABLE 1

4-Day OVX Rat Assay

| Compound # | Dose mg/kg | Uterine Wt. % inc. OVX | Uterine EPO (V max) | Cholest % dec. OVX |
|---|---|---|---|---|
| EE2 | 0.1 | 223.2* | 265.2* | 91.2* |
| Example 5 | .01 | 33.8* | 4.2 | 65.5* |
|  | .1 | 45.7* | 4.8 | 55.6* |
|  | 1 | 121.3* | 63.4* | 90.2* |
| Example 7 | .01 | 1.5 | 3.6 | 41.3* |
|  | .1 | 11 | 3 | 48.3* |
|  | 1 | 40.5* | 2.4 | 58.8* |
| Example 9 | .01 | −3.3 | 3.7 | 31.4* |
|  | .1 | 10.5 | 4.6 | 33.4* |
|  | 1 | −5 | 3.7 | 37.3* |
| Example 10 | .01 | 7 | 2.4 | 30.4* |
|  | .1 | −8.3 | 1.9 | 31.3* |
|  | 1 | 20.9 | 2.6 | 20.9 |
| Example 12 | .01 | −14.2 | 2.0 | 18.1 |
|  | .1 | −0.3 | 2.5 | 38.0* |
|  | 1 | 46.5* | 9.0 | 58.9* |
| Example 3 | .01 | 102 | 2.9 | 11.8 |
|  | .1 | 17.2 | 2.3 | 27.2* |
|  | 1 | 67.7* | 16.0* | 58.6* |
| Example 13 | .01 | −12.2 | 2.2 | 12 |
|  | .1 | −25.2* | 1.9 | 78.9* |
|  | 1 | 51.3* | 39.2 | 100* |
| Example 15 | .01 | −19 | 3.0 | 10.2 |
|  | .1 | −23.5 | 4.0 | 32.8* |
|  | 1 | 63.3* | 121.7* | 92.1* |
| Example 17 | .01 | −33.9* | 1.6 | 10.2 |
|  | .1 | −3.6 | 7.8 | 32.8* |
|  | 1 | 54.5* | 279.6* | 92.1* |
| Example 18 | .01 | −0.9 | 2.8 | 10.3 |
|  | .1 | 24.4 | 3.2 | 71.8* |
|  | 1 | 73.9* | 2.9 | 100* |

In addition to the demonstrated benefits of the compounds of the instant invention, the above data clearly demonstrate that compounds of Formula I are not estrogen mimetics.

Furthermore, no deleterious toxicological effects (for example, survival numbers) were observed with any treatment.

Osteoporosis Test Procedure

Following the General Preparation Procedure, infra, the rats are treated daily for 35 days (6 rats per treatment group) and sacrificed by carbon dioxide asphyxiation on the 36th day. The 35 day time period is sufficient to allow maximal reduction in bone density, measured as described herein. At the time of sacrifice, the uteri are removed, dissected free of extraneous tissue, and the fluid contents expelled before determination of wet weight in order to confirm estrogen deficiency associated with complete ovariectomy. Uterine weight is routinely reduced about 75% in response to ovariectomy. The uteri are then placed in 10% neutral buffered formalin to allow for subsequent histological analysis.

The right femurs are excised and digitilized x-rays generated and analyzed by an image analysis program (NIH image) at the distal metaphysis. The proximal aspect of the tibiae from these animals are also scanned by quantitative computed tomography.

In accordance with the above procedures, compounds of the instant invention and ethynyl estradiol ($EE_2$) in 20% hydroxypropyl β-cyclodextrin are orally administered to test animals. Results from distal femur metaphysis and proximal tibiae data are reported as percent protection relative to ovariectomy.

We claim:

1. A compound of formula

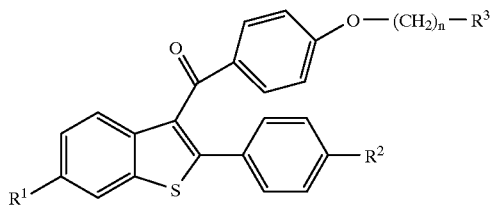

I wherein:

$R^1$ is —H, —OH, —O($C_1$–$C_4$ alkyl), —OCO($C_1$–$C_6$ alkyl), —O(CO)O($C_1$–$C_6$ alkyl), —OCOAr, —O(CO)OAr, where Ar is phenyl or optionally substituted phenyl, or —$OSO_2$($C_2$–$C_6$ alkyl);

$R^2$ is —H, —OH, —O($C_1$–$C_4$ alkyl), —OCO($C_1$–$C_6$ alkyl), —O(CO)O($C_1$–$C_6$ alkyl), —OCOAr, —O(CO)OAr, where Ar is phenyl or optionally substituted phenyl, or —$OSO_2$($C_2$–$C_6$ alkyl);

$R^3$ is —$CH_3$, thiophenyl, thiazolyl or optionally substituted thiazolyl, phenyl or optionally substituted phenyl, 2-pyridyl, 3-pyridyl, 4-pyridyl, or cyclohexyl; and n is 0 to 10;

with the proviso that when $R^1$ or $R^2$ is —OH or —O($C_1$–$C_4$ alkyl) and $R^3$ is —$CH_3$, then n is 7–10; and with the further proviso that when $R^1$ or $R^2$ is —H, —OH, —O($C_1$–$C_4$ alkyl), —OCO ($C_1$–$C_6$ alkyl), or —OCOAr and $R^3$ is thiophenyl thiazolyl, optionally substituted thiazolyl, 2-pyridyl, 3-pyridyl, or 4-pyridyl, then n is 0 or n is 8–10;

or a pharmaceutically acceptable salt or solvate thereof.

2. A compound according to claim 1 wherein $R^1$ is hydroxy.

3. A compound according to claim 1 wherein $R^1$ is methoxy.

4. A compound according to claim 1 wherein $R^2$ is hydroxy.

5. A compound according to claim 1 wherein $R^2$ is methoxy.

6. A compound according to claim 1 wherein n is two.

7. A compound according to claim 1 wherein n is 3 to 10.

8. A compound according to claim 1 wherein n is 4 to 10.

9. A compound according to claim 1 wherein $R^3$ is thiazolyl.

10. A compound according to claim 1 wherein $R^3$ is thiophene.

11. A compound according to claim 1 wherein $R^3$ is selected from the group consisting of 2-pyridyl, 3-pyridyl, and 4-pyridyl.

12. A compound according to claim 1 wherein $R^1$ and $R^2$ are methoxy.

13. A compound according to claim 1 wherein the salt thereof is the hydrochloride salt.

14. A compound according to claim 1 selected from the group consisting of

[6-Methoxy-2-(4-methoxyphenyl)benzo[b]thien-3-yl][4-(2-(cyclohexyl)ethoxy]phenyl]methanone;

[6-Hydroxy-2-(4-hydroxyphenyl)benzo[b]thien-3-yl][4-(2-(cyclohexyl)ethoxy]phenyl]methanone;

[6-Hydroxy-2-(4-hydroxyphenyl)benzo[b]thien-3-yl][4-(n-decyloxy]phenyl]methanone;

[6-Methoxy-2-(4-methoxyphenyl)benzo[b]thien-3-yl][4-[4-(fluoro)benzyloxy]phenyl]methanone;

[6-Methoxy-2-(4-methoxyphenyl)benzo[b]thien-3-yl][4-[4-(methoxy)benzyloxy]phenyl]methanone;

[6-Methoxy-2-(4-methoxyphenyl)benzo[b]thien-3-yl][4-[2-(4-methoxy)phenyl]ethoxy]phenyl]methanone; and

[6-hydroxy-2-(4-hydroxyphenyl)benzo[b]thien-3-yl][4-[2-(4-hydroxy)phenyl]ethoxy]phenyl]methanone.

15. A pharmaceutical formulation comprising a compound according to claim 1, or a pharmaceutically acceptable salt or solvate thereof, in combination with a pharmaceutically acceptable carrier, diluent, or excipient.

16. A method of inhibiting bone loss or bone resorption which comprises administering to a patient in need thereof an effective amount of a compound of claim 1.

17. A method according to claim 16, wherein said bone loss or bone resorption is due to menopause or ovariectomy.

18. A method of lowering serum cholesterol levels which comprises administering to a patient in need thereof an effective amount of a compound of claim 1.

* * * * *